United States Patent [19]
Herstein et al.

[11] Patent Number: 5,840,309
[45] Date of Patent: Nov. 24, 1998

[54] STIMULATING FIBROBLASTS AND/OR KERATINOCYTES

[75] Inventors: Morris Herstein, Scarsdale, N.Y.; Marion Froschle, Volketswil, Switzerland

[73] Assignee: La Prairie SA, Volketswil, Switzerland

[21] Appl. No.: 779,171

[22] Filed: Jan. 6, 1997

Related U.S. Application Data

[63] Continuation of Ser. No. 317,144, Oct. 3, 1994, abandoned.

[51] Int. Cl.⁶ .......................... A61K 35/78; A61K 35/72; A61K 35/74
[52] U.S. Cl. .................. 424/195.1; 424/520; 424/93.45; 424/93.51
[58] Field of Search ................................ 424/520, 195.1, 424/93.45, 93.51

[56] References Cited

FOREIGN PATENT DOCUMENTS

| | | |
|---|---|---|
| 2265401 | 10/1975 | France . |
| 2273551 | 1/1976 | France . |
| 2696932 | 4/1994 | France . |
| 6065041 | 3/1994 | Japan . |

OTHER PUBLICATIONS

Cell and Tissue Research, 1988, 253:657–663.

*Primary Examiner*—Jean C. Witz
*Attorney, Agent, or Firm*—Sprung Kramer Schaefer & Briscoe

[57] ABSTRACT

A method of stimulating at least one of fibroblasts and keratinocytes in an individual in need thereof which comprises applying to such individual an amount effective therefor of a composition comprising A) glycoprotein 1
B) glycoprotein 2
C) ginseng extract, and
D) horsetail extract.

6 Claims, No Drawings

STIMULATING FIBROBLASTS AND/OR KERATINOCYTES

This application is a continuation of application Ser. No. 08/317,144, filed Oct. 3, 1994, now abandoned.

The present invention relates to novel compositions for stimulating at least one of fibroblasts and keratinocytes.

By such stimulations it is known that cellular metabolism will be increased with production of new cells, enhancement of the natural capacity of cells to survive and reproduce, and supplying energy to the skin cells. As a result the skin appears more radiant and vibrant, i.e. younger looking.

Various materials have heretofore been applied to skin to stimulate the fibroplasts or keratinocytes with varying degrees of success and failure.

For example, Brysk et al in Cell Tissue Res. (1988) 253: 657–663 disclose that glycoproteins modulate adhesion in terminally differentiated keratinocytes.

It is an object of the present invention to provide compositions which stimulate either or preferably both the fibroblasts and keratinocytes in a manner and to an extent not heretofore possible.

This and other objects and advantages are realized in accordance with the present invention pursuant to which there are provided certain combinations of known materials which synergize and provide a more than additive effect. Moreover, they provide effects not even possible with the individual materials alone or in only partial combination.

Pursuant to the invention there is provided a composition synergistically stimulating at least one of fibroblasts and keratinocytes, comprising A) glycoprotein 1
B) glycoprotein 2
C) ginseng extract, and
D) horsetail extract.

Advantageously there are present about 5 to 40, preferably about 20, parts of A,
25 to 8, preferably about 50, parts of B,
1 to 10, preferably about 5, parts of C, and
1 to 10, preferably about 5, D.

Advantageously the weight ratio of A+B: C+D ranges from about 1:2 to 1:4 preferably about 1:3, and the weight ratio of C:D is from about 3:1 to 1:3.

The composition can be applied to the face, eyelids or other body parts in an amount varying with the individual. About 0.01 to 1, advantageously about 0.02 to 0.75 and preferably about 0.3 to 0.5, grams per cm$^2$ has been found useful but more or less can be used. The application can be once weekly or more often, even several times a day.

The composition includes the recited components in a total amount of about 0.5 to 50 grams per liter, preferably about 3 to 10 grams per liter, although higher or lower concentrations are permissible. Such compositions being in the form of an emulsion, cream, salve or the like, the active materials being admixed with water, alkylene glycols, various oils natural and synthetic, petrolatum, preservatives, coloring agents, perfumes, and like ingredients conventional in the cosmetic arts.

Returning to the novel composition, glycoprotein 1 (GP1) is commercially available and comprises a purified cytoplasmatic fraction obtained from yeast and saccharomyces. It comprises a mixture of amino acids, nucleic acids, nucleotides, carbohydrates, lipids, oligo elements, vitamins and phosphatase enzymes.

Glycoprotein 2 (GP2) is also commerically available and comprises a purified cytoplasmatic fraction obtained from Lactobacillus, comprising a mixture of amino acids, nucleic acids, nucleotides, carbohydrates, lipids, oligo elements, vitamins and phosphatase enzymes.

Ginseng is an extract obtained by extracting with a solvent (water, ethanol, glycol or mixtures thereof) the root of Panax ginseng. It contains saponins, sterols, carbohydrates, pectin, vitamins, minerals and lipids.

Horsetail is an extract obtained by extracting with a solvent (water, ethanol, glycol or mixtures thereof) the whole herb of *Equisetum arvense* Linne. It contains silicates, flavinoids, saponosides, caffeic acid and ferulic acid.

The invention will be further described in the following illustrative examples wherein all parts are by weight unless otherwise expressed. GP 1 identifies glycoprotein 1 hereinabove GP 2, glycoprotein 2, G ginseng and H horsetail extract. Thus, "GP 12/GH 12% (25:75)" example, means a mixture of all four, containing 3% GP 1, 6% GP 2, 1.5% G and 1.5% H.

EXAMPLE 1
FACIAL MOISTURIZER

| Composition | % W/W |
|---|---|
| PART A: | |
| Purified Water | 49.403 |
| Carbomer 940 | 0.150 |
| Pemulen TR-1 | 0.250 |
| Keltrol T | 0.060 |
| 1,3 Butylene Glycol | 3.000 |
| Glycerin | 15.000 |
| Allantoin | 0.050 |
| O-Phenylphenol | 0.150 |
| Methylparaben | 0.250 |
| Propylparaben | 0.150 |
| PART B: | |
| Octyldodecyl Myristate | 4.000 |
| Isopropyl Palmitate | 2.000 |
| Octyl Methoxycinnamate | 2.500 |
| DC 200/5 | 1.500 |
| Tocopheryl Acetate | 0.050 |
| Retinyl Palmitate | 0.050 |
| Arlacel 80 | 0.100 |
| BHT | 0.100 |
| DC 345 Fluid | 18.000 |
| PART C: | |
| Triethanolamine (99%) | 0.350 |
| PART D: | |
| Nylon-12 | 2.000 |
| PART E: | |
| GP12/GH | 0.300 |
| PART F: | |
| Sodium Hyaluronate | 0.500 |
| PART G: | |
| Fragrance | 0.050 |
| PART H: | |
| FD&C Yellow No. 5 | 0.017 |
| Water | 0.020 |

MANUFACTURING PROCEDURE
PART A

1. Into a suitably sized stainless steel tank (jacketed) and equipped with lightning mixer and sweep agitation add the purified water and heat to 70°–75° C. Add the Carbomer and mix until a smooth dispersion is obtained.

2. Add the balance of the Phase A ingredients. Mix with moderate agitation and maintain at 70°–75° C.

PART B

1. Into a separate stainless steel jacketed kettle equipped with a lightning mixer add the ingredients in part B in sequence and heat to 70°–75° C. with moderate agitation.

2. When Part B is fully dissolved and at 70° C., add it to Part A with moderate agitation.

PART C

1. Add Part C while mixing and then change to sweep agitation and start cooling.

2. Cool to 40° C.

PART D

1. Add part D while mixing and maintain at 40° C.

PART E

1. Add Part E while mixing at 40° C.

PART F

1. Add Part F while mixing at 40° C.

PART G

1. Add Part G while mixing at 40° C.

PART H

1. Add Part H while mixing at 40° C. Homogenize or colloid mill bulk at 40° C.

2. Cool to 25° C.

EXAMPLE 2
EYE CREAM

| COMPOSITION: | % W/W |
|---|---|
| PHASE A: WATER PHASE | 59.944 |
| Water | |
| Propylene Glycol | 3.000 |
| Methylparaben | 0.250 |
| Carbopol 934 | 0.500 |
| PHASE B: OIL PHASE | |
| Dicaprylyl Maleate | 4.000 |
| Hydrogenated Isobutene | 6.500 |
| Hydrogenated Vegetable Oil | 3.000 |
| Acetylated Lanolin | 3.500 |
| Propylparaben | 0.013 |
| Ethylparaben | 0.038 |
| DEA-Cetyl Phosphate | 0.500 |
| Petrolatum | 4.800 |
| Xalifin 15 | 9.000 |
| PHASE C: NEUTRALIZING | |
| Water | 1.000 |
| Triethanolamine | 0.500 |
| PHASE E: INGREDIENTS #1 | |
| Water | 1.700 |
| GP12/GH | 0.300 |
| PHASE F: PRESERVATIVE | |
| Water | 1.000 |
| Germall 115 | 0.250 |
| PHASE G: FRAGRANCE | 0.205 |

MANUFACTURING PROCEDURE

PART A

1. Into a suitably sized stainless steel tank (jacketed) and equipped with lightning mixer and sweep agitation add the Purified Water and heat to 70°–75° C. Add the Carbopol and mix until a smooth dispersion is obtained.

2. Add the balance of the Phase A ingredients. Mix with moderate agitation and maintain at 70°–75° C.

PART B

1. Into a separate stainless steel jacketed kettle equipped with a lightning mixer add the ingredients in part B in sequence and heat to 70°–75° C. with moderate agitation.

2. When Part B is fully dissolved and at 70° C. add it to Part A with moderate agitation and homogenization. Cool the bulk to 40° C.

PART C

1. Add Part C while mixing.

PART D

1. Add Part D while mixing and maintain cooling at 40° C.

PART E

1. Add part E while mixing at 40° C.

PART F

1. Add Part F while mixing at 40° C.

PART G

1. Add Part G while mixing at 40° C. Homogenize as in a colloid mill at 40° C.

2. Cool to 25° C.

EXAMPLE 3
ANTIWRINKLE CREAM

| | % W/W |
|---|---|
| PHASE A: WATER PHASE | |
| Water | 22.299 |
| Propylene Glycol | 2.000 |
| Methylparaben | 0.450 |
| Sodium Borate | 0.500 |
| Aerosil 200 | 1.500 |
| PHASE B: OIL PHASE | |
| Dicaprylyl Maleate | 8.000 |
| Hydrogenated Polyisobutene | 15.600 |
| Vegetable Oil | 9.000 |
| Acetylated Lanolin | 5.000 |
| Propylparaben | 0.038 |
| Ethylparaben | 0.113 |
| BHT | 0.020 |
| Cholesterol | 0.250 |
| Elfacos ST 37 | 2.000 |
| Amphisol | 0.300 |
| Petrolatum | 9.900 |
| Beeswax | 7.000 |
| Miglyol Gel B | 10.500 |
| PHASE C: Water | 3.430 |
| GP12/GH | 0.300 |
| PHASE D: Water | 1.000 |
| Germall 115 | 0.300 |
| PHASE E: Fragrance | 0.500 |

MANUFACTURING PROCEDURE

Part A

1. Into a suitably sized stainless steel tank (jacketed) and equipped with lightning mixer and sweep agitation add the purified water and heat to 70°–75° C. Add the Aerosil 200 and mix until a smooth dispersion is obtained.

2. Add the balance of the Phase A ingredients. Mix with moderate agitation and maintain at 70°–75° C.

PART B

1. Into a separate stainless steel jacketed kettle equipped with a lightning mixer add the ingredients in part B in sequence and heat to 70°–75° C. with moderate agitation.

2. When Part B is fully dissolved and at 70° C., add it to Part A with moderate agitation and homogenization. Cool to 40° C.

PART C

1. Add Part C while mixing at 40° C.

PART D

1. Add Part D while mixing and maintain cooling at 40° C.

PART E

1. Add Part E while mixing at 40° C. Homogenize or colloid mill at 40° C.

2. Cool to 25° C.

For assaying the performance of the novel compositions the following in vitro comparison trials were carried out using compositions free of additives to permit clearer evaluation.

The tests were conducted as follows:

| Title: Neutral Red Assay | | |
|---|---|---|
| 1.0 | Purpose | To assay cells for toxicity from exposure to test samples |
| 2.0 | Definitions | Neutral Red (3-amino-7-dimothylamino-2-methylphenazine hydrochloride)-active uptake, biological dye |
| 3.0 | Materials | |
| | Neutral Red Sigma (or equivalent) | |
| | Dulbecco's Modified Eagles Media GIBCO (or equivalent) | |
| | Bovince Calf Serum GIBCO (or equivalent) | |
| | 96-well flat bottom tissue culture plate Falcon (or equivalent | |
| | 1% Formaldehyde/1% $CaCl_2$ Sigma (or equivalent) | |
| | PBS (Phosphate Buffered Saline) | |
| | Acetic Acid/EtOH Sigma (or equivalent) | |
| | Dynatech microtiter plate reader | |
| | Quadraplates | |
| | Multichannel pipet | |
| | pipet tips | |
| | NUNC plate washer | |
| | Coulter counter | |
| | Phase contrasting microscope | |
| 4.0 | Procedure | |
| | 4.1 | Plate normal human dermal fibroblasts (ATCC or Clonetics; adult or neonatal; specified) in 10% FBS/DMEN/penstrep/1-glutamine in a 96 well flatbottom tissue culture plate at 3000 cells per well. |
| | | 4.4.1 Dilute cells to a stock concentration of $1.5 \times 10^4$ cells/ml and add 200 ul per well. |
| | | 4.4.2 Incubate cells 72–96 hours-until cells are ~80% confluent. |
| | 4.3 | Prepare dilution of sample to be tested in 1% BCS/DMEM and sore at 40° C. until needed. |
| | | 4.3.1 Filter using 0.22 n syringe filter. |
| | | 4.3.2 If needed, prefilter with a 0.45 u filter. |
| | 4.4 | After fibroblasts have come to the desired confluency, aspirate off growth media using NUNC washer. |
| 4.5 | Add 200 ul/well of 1% BCS/DMEM, and incubate for 24 hours at 37° C./5% $CO_2$. | |
| 4.6 | Aspirate off growth media using NUNC washer. | |
| | | 4.6.1 Add 200 ul of test sample per well in quadruplicate. |
| | | 4.6.2 Incubate plate for appropriate exposure time (e.g. 1 hr–24 hr) at 37° C./5% $CO_2$. |
| 4.7 | After incubation period, aspirate off test sample using NUNC wash. | |
| 4.8 | Add 200 ul/well of 50 ug/ml NR solution. | |
| | | 4.8.1 To prepare 50 ug/ml solution from 3.0 mg/ml stock: |
| | | 4.8.1.1 (3000 ug/ml) (x) = (50 ug/ml) (20 ml) x = 333 ul stock solution + 19.67 ml 1% media |
| | | 4.8.2 Incubate for 3–4 hours at 3% C/5% $CO_2$. |
| | | 4.8.3 Prepare 1% formaldehyde/1% $CaCl_2$ solution: |
| | | 4.8.3.1 (37% formaldehyde) (x) = (1% formaldehyde) (500 ml) x = 13.5 ml of 37% formaldehyde + 486.5 ml $H_2O$ plus 5 grams of $CaCl_2$ to the 500 ml solution. |
| | | 4.8.4 Prepare 1% Acetic acid/50% Ethanol solution: |
| | | 4.8.4.1 (95% EtOH) (x) = (50% EtOH) (500 ml) x = 263.2 ml of 95% EtOH + 231.8 ml $H_2O$ plus 5.0 ml glacial acetic acid |
| 4.9 | After 3 hour incubation, aspirate off NR. | |
| | | 4.9.1 Using squirt bottle, add 1% formaldehyde/1% $CaCl_2$ solution by gently filling wells. This can be done at the sink. |
| | | 4.9.2 Aspirate off formaldehyde. |
| | | 4.9.3 Gently wash 2x with PBS using squirt bottle. |
| | | 4.9.4 Add 100 ul of Acetic Acid/EtOH solution per well using multichannel pipet. |
| | | 4.9.5 Incubate 20 minutes at RT, shaking on a plate shaker. |
| 4.10 | Read plate on Dynatech microplate reader at 570 nm. | |
| | | 4.10.1 Set-up template on reader to calculate averages/standard deviations of replicates. |

| Title: Neutral Red Assay | | |
|---|---|---|
| 5.0 | Analysis | |
| | 5.1 | Transfer averaged OD and standard deviation values into an Excel spread sheet |
| | | 5.1.1 Calculate: average OD test sample x 100 = % of untreated control average OD control |
| | | 5.1.2 The Neutral Red 50 endpoint is read on the x-axis where the curve intercepts 50% of the untreated control. |

The results obtained were as follows:

LEGEND

| GP1 | GLYCOPROTEIN #1 |
|---|---|
| GP2 | GLYCOPROTEIN #2 |
| GP12/GH | MIXTURE OF GP1 & GP2 IN VARYING RATIOS WITH G & H |
| G | GINSENG EXTRACT |
| H | HORSETAIL EXTRACT |
| GP2/GH | MIXTURE OF GP2 & G & H |

TABLE # 1

| | | | PER CENT CHANGE IN PROLIFERATION | |
|---|---|---|---|---|
| | | | FIBROBLASTS | KERATINOCYTES |
| GP12/GH | 12% | (25:75) | +13.5 | +9.3 |
| GP12/GH | 12% | (50:50) | +14.8 | −24.3 |
| GP12/GH | 12% | (75:25) | +14.1 | −41.7 |
| GP1 | 3% | | −17.0 | −31.3 |
| GP2 | 6% | | −7.3 | −0.7 |
| GP2/GH | 9% | | +2.1 | −12.6 |
| G | 0.6 | | −45.3 | −14.3 |
| H | 0.6 | | −44.6 | −33.3 |

TABLE # 2

| GP12/GH | 6% | (25:75) | +2.5 | +9.1 |
|---|---|---|---|---|
| GP12/GH | 6% | (50:50) | +45.4 | −16.9 |
| GP12/GH | 6% | (75:25) | +35.3 | −15.7 |
| GP1 | 1.5% | | −11.8 | −21.1 |
| GP2 | 1.2% | | +31.8 | −2.1 |
| GP2/GH | 4.5% | | 0 | −5.5 |
| G | 0.12 | | −3.8 | −2.8 |
| H | 0.12 | | +64.7 | −22.1 |

TABLE # 3

| GP12/GH | 1.2% | (25:75) | +12.8 | +11.8 |
|---|---|---|---|---|
| GP12/GH | 1.2% | (50:50) | +38.6 | +0.4 |
| GP12/GH | 1.2% | (75:25) | +46.4 | −18.4 |
| GP1 | 0.3% | | −4.8 | +8.8 |
| GP2 | 0.6% | | +11.4 | −5.0 |
| GP/2GH | 0.9% | | +1.5 | +20.5 |

TABLE # 4

| | | | PER CENT CHANGE IN PROLIFERATION | |
|---|---|---|---|---|
| | | | FIBROBLASTS | KERATINOCYTES |
| GP12/GH | 0.6% | (25:75) | +21.3 | +17.9 |
| GP12/GH | 0.6% | (50:50) | +28.7 | +0.3 |
| GP12/GH | 0.6% | (75:25) | +51.0 | −16.0 |

TABLE # 4-continued

|  |  | PER CENT CHANGE IN PROLIFERATION | |
|---|---|---|---|
|  |  | FIBROBLASTS | KERATINOCYTES |
| GP1 | 0.15% | +2.1 | +2.3 |
| GP2 | 0.12 | +41.9 | −5.0 |
| GP2/GH | 0.45% | +4.0 | +13.3 |

TABLE # 5

FACIAL MOISTURIZER

|  |  |  | PER CENT CHANGE IN PROLIFERATION | |
|---|---|---|---|---|
|  |  |  | FIBROBLASTS | KERATINOCYTES |
| GP12/GH | 0.06% | (25:75) | +43.5 | −17.3 |
| GP12/GH | 0.3% | (25:75) | +64.6 | −2.3 |
| GP12/GH | 0.6% | (25:75) | +65.9 | −22.4 |
| GP12/GH | 3% | (25:75) | +54.3 | −11.0 |
| GP12/GH | 6% | (25:75) | +13.5 | +133.2 |

EYE CREME

| GP12/GH | 0.06% | (25:75) | +7.6 | −24.6 |
|---|---|---|---|---|
| GP12/GH | 0.3% | (25:75) | +34.8 | −23.8 |
| GP12/GH | 0.6% | (25:75) | +11.4 | −28.3 |
| GP12/GH | 3% | (25:75) | −6.5 | −44.7 |
| GP12/GH | 6% | (25:75) | −31.8 | −7.4 |

ANTIWRINKLE CREAM

| GP12/GH | 0.06% | (25:75) | +22.6 | −14.7 |
|---|---|---|---|---|
| GPI2/GH | 0.3% | (25:75) | +36.9 | −10.0 |
| GP12/GH | 0.6% | (25:75) | +11.2 | −20.8 |
| GP12/GH | 3% | (25:75) | −24.5 | −54.8 |
| GP12/GH | 6% | (25:75) | −45.6 | −51.6 |

TABLE # 6

GP12/GH VARY CONC. (25:75):

|  |  |  | PER CENT CHANGE IN PROLIFERATION | |
|---|---|---|---|---|
|  |  |  | FIBROBLASTS | KERATINOCYTES |
| GP12/GH | 12% | (25:75) | +13.5 | +9.3 |
| GP12/GH | 6% | (25:75) | +2.5 | +9.1 |
| GP12/GH | 1.2% | (25:75) | +12.8 | +11.8 |
| GP12/GH | 0.6% | (25:75) | +21.3 | +17.9 |

TABLE # 7

GP12/GH VARY CONC. (50:50):

|  |  |  | PER CENT CHANGE IN PROLIFERATION | |
|---|---|---|---|---|
|  |  |  | FIBROBLASTS | KERATINOCYTES |
| GP12/GH | 12% | (50:50) | +14.8 | −24.3 |
| GP12/GH | 6% | (50:50) | +45.4 | −16.9 |
| GP12/GH | 1.2% | (50:50) | +38.6 | +0.4 |
| GP12/GH | 0.6% | (50:50) | +28.7 | +0.3 |

TABLE # 8

GP12/GH VARY CONC. (75:25):

|  |  |  | PER CENT CHANGE IN PROLIFERATION | |
|---|---|---|---|---|
|  |  |  | FIBROBLASTS | KERATINOCYTES |
| GP12/GH | 12% | (75:25) | +14.1 | −41.7 |
| GP12/GH | 6% | (75:25) | +35.3 | −15.7 |
| GP12/GH | 1.2% | (75:25) | +46.4 | −18.4 |
| GP12/GH | 0.6% | (75:25) | +51.0 | −16.0 |

TABLE # 9

GP1:

|  |  | PER CENT CHANGE IN PROLIFERATION | |
|---|---|---|---|
|  |  | FIBROBLASTS | KERATINOCYTES |
| GP1 | 3% | −17.0 | −31.3 |
| GP1 | 1.5% | −11.8 | −21.1 |
| GP1 | 0.3% | −4.8 | +8.8 |
| GP1 | 0.15% | +2.1 | +2.3 |

TABLE # 10

GP2:

|  |  | PER CENT CHANGE IN PROLIFERATION | |
|---|---|---|---|
|  |  | FIBROBLASTS | KERATINOCYTES |
| GP2 | 6% | −7.3 | −0.7 |
| GP2 | 1.2% | +31.8 | −2.1 |
| GP2 | 0.6% | +11.4 | −5.0 |
| GP2 | 0.12 | +41.9 | −5.0 |

TABLE # 11

GP2/GH:

|  |  | PER CENT CHANGE IN PROLIFERATION | |
|---|---|---|---|
|  |  | FIBROBLASTS | KERATINOCYTES |
| GP2/GH | 9% | +2.1 | −12.6 |
| GP2/GH | 4.5% | 0 | −5.5 |
| GP/2GH | 0.9% | +1.5 | +20.5 |
| GP2/GH | 0.45% | +4.0 | +13.3 |

Tables 1 and 2, for example, at their right show that the individual components have from slightly negative to highly negative effects on keratinocytes but the first four component mixture of each of those tables has a positive effect, i.e. from multiple negatives to a positive effect. This goes beyond synergy.

Similarly in many instances the effect on fibroblasts converts from multiple negatives to a positive.

Even more important, in many instances the new compositions have significant positive effects on both fibroblasts and keratinocytes simultaneously, e.g. the first line of horizontal entries in each of Tables 1 to 4 and 6.

The tables also include data for compositions containing fewer than all four active ingredients, i.e. for compositions which are not GP12/GH. Further, the tables contain an occassional anomalous result, as is to be expected when dealing with testing of biological compositions.

It will be appreciated that the instant specification and the claims are set forth by way of illustration and not limitation, and that various modifications and changes may be made without departing from the spirit and scope of the present invention.

We claim:

1. A composition for stimulating at least one of fibroblasts and keratinocytes comprising a synergistically effective amount therefor of a combination of the following ingredients:
   a) glycoprotein 1, which is a purified cytoplasmic fraction obtained from yeast and Saccharomyces;
   b) glycoprotein 2, which is a purified cytoplasmic fraction obtained from Lactobacillus,
   c) ginseng extract; and
   d) horsetail extract.

2. The composition according to claim 1, wherein the ratio of glycoprotein 1 to the combination of glycoprotein 2, ginseng extract, and horsetail extract is about 25:75.

3. The composition according to claim 2, which comprises glycoprotein 1, glycoprotein 2, ginseng extract, and horsetail extract in a range of about 0.3 to about 1.2% by weight of the total weight of the composition.

4. A method of stimulating at least one of fibroblasts and keratinocytes in an individual in need thereof which comprises applying to such individual an amount effective therefor of a composition according to claim 1.

5. The method according to claim 4, wherein said composition the ratio of glycoprotein 1 to the combination of glycoprotein 2, ginseng extract, and horsetail extract is about 25:75.

6. The method according to claim 5, wherein said composition comprises glycoprotein 1, glycoprotein 2, ginseng extract, and horsetail extract in a range of about 0.3 to about 1.2% by weight of the total weight of the composition.

* * * * *